US012605176B2

(12) United States Patent
Ibrahim et al.

(10) Patent No.: US 12,605,176 B2
(45) Date of Patent: Apr. 21, 2026

(54) LEFT ATRIAL APPENDAGE MANIPULATION AND TRACTION

(71) Applicant: AtriCure, Inc., Mason, OH (US)

(72) Inventors: Tamer Ibrahim, Danville, CA (US); Dwight P. Morejohn, Davis, CA (US); Matthew Monti, Cincinnati, OH (US); Michael J. Banchieri, Discovery Bay, CA (US); Ara M. Stephanian, Davis, CA (US); Kenneth L. Miller, Hamilton, OH (US)

(73) Assignee: AtriCure, Inc., Mason, OH (US)

( * ) Notice: Subject to any disclaimer, the term of this patent is extended or adjusted under 35 U.S.C. 154(b) by 687 days.

(21) Appl. No.: 16/751,150

(22) Filed: Jan. 23, 2020

(65) Prior Publication Data

US 2020/0229837 A1      Jul. 23, 2020

Related U.S. Application Data

(60) Provisional application No. 62/795,992, filed on Jan. 23, 2019.

(51) Int. Cl.
  *A61B 17/30*        (2006.01)
  *A61B 17/12*        (2006.01)
      (Continued)

(52) U.S. Cl.
  CPC ........ *A61B 17/30* (2013.01); *A61B 17/12122* (2013.01); *A61B 17/122* (2013.01);
      (Continued)

(58) Field of Classification Search
  CPC . A61B 17/30; A61B 17/12122; A61B 17/122; A61B 17/1285; A61B 17/00234;
      (Continued)

(56) References Cited

U.S. PATENT DOCUMENTS 5,286,255  A      2/1994  Weber
6,152,936  A  *  11/2000  Christy ............ A61B 17/12013
                                                606/139

(Continued)

FOREIGN PATENT DOCUMENTS

JP        H05184588 A      7/1993

*Primary Examiner* — Richard G Louis
(74) *Attorney, Agent, or Firm* — Dorton & Willis LLP; Ryan Willis

(57)            ABSTRACT

A method of positioning an occlusion clip proximate a left atrial appendage may include creating an access port that exposes the left atrial appendage; delivering a suction grasper via the access port, the suction grasper including opposing jaws each having a suction port; delivering an occlusion clip via the access port; grasping the left atrial appendage via the suction grasper by applying suction to an exterior of the left atrial appendage so that a portion of the left atrial appendage interposes the opposing jaws while suction is applied via the suction ports; repositioning the suction grasper to tension the left atrial appendage; delivering an occlusion clip via the access port; clamping a base of the left atrial appendage using the occlusion clip while the suction grasper applies tension to the left atrial appendage; and/or egressing the suction grasper via the access port.

18 Claims, 11 Drawing Sheets

(51) Int. Cl.
    *A61B 17/122*     (2006.01)
    *A61B 17/128*     (2006.01)
    *A61B 17/00*     (2006.01)

(52) U.S. Cl.
    CPC .............................. *A61B 17/1285* (2013.01);
    *A61B 2017/00632* (2013.01); *A61B 2017/306*
    (2013.01)

(58) Field of Classification Search
    CPC ................ A61B 17/064; A61B 17/083; A61B
        17/12013; A61B 17/12131; A61B 17/221;
        A61B 17/00491; A61B 17/12031; A61B
        2017/00632; A61B 2017/306; A61B
        2017/308; A61B 2017/00243; A61B
        2217/005
    See application file for complete search history.

(56)            References Cited

U.S. PATENT DOCUMENTS

| | | | |
|---|---|---|---|
| 6,537,289 B1 * | 3/2003 | Kayan .................. | A61B 17/122 606/157 |
| 7,645,285 B2 * | 1/2010 | Cosgrove ............... | A61B 17/12 606/151 |
| 8,636,754 B2 | 1/2014 | Hughett, Sr. et al. | |
| 9,017,349 B2 | 4/2015 | Privitera et al. | |
| 9,861,371 B2 | 1/2018 | Martin et al. | |
| 9,883,867 B2 | 2/2018 | Martin et al. | |
| 9,901,351 B2 | 2/2018 | Winkler et al. | |
| 9,901,352 B2 | 2/2018 | Fago et al. | |
| 10,201,352 B2 | 2/2019 | Fago et al. | |
| 2006/0020271 A1 * | 1/2006 | Stewart ............ | A61B 17/12013 606/139 |
| 2008/0255427 A1 * | 10/2008 | Satake ................... | A61B 17/08 606/205 |
| 2011/0077672 A1 * | 3/2011 | Fleischman ........ | A61B 17/0401 606/232 |
| 2012/0172924 A1 * | 7/2012 | Allen, IV ............... | A61B 17/29 606/205 |
| 2016/0249932 A1 * | 9/2016 | Rogers ............... | A61B 17/0469 606/144 |
| 2017/0340335 A1 * | 11/2017 | Ad ..................... | A61B 17/0057 |
| 2019/0142428 A1 | 5/2019 | Widenhouse et al. | |
| 2019/0192178 A1 * | 6/2019 | Batchelor ......... | A61B 18/1445 |

* cited by examiner

16

12

24

20

22

LEFT ATRIAL APPENDAGE MANIPULATION AND TRACTION

CROSS REFERENCE TO RELATED APPLICATIONS

This application claims the benefit of U.S. Provisional Application No. 62/795,992, filed Jan. 23, 2019, which is incorporated by reference.

INTRODUCTION TO THE INVENTION

The present disclosure is directed to medical devices and related methods, and, more specifically, to devices for manipulating and/or applying traction to anatomical structures, such as a left atrial appendage of a heart, and related methods.

The present disclosure contemplates that atrial fibrillation is a common heart arrhythmia, affecting millions of people in the United States. The present disclosure contemplates that, in some circumstances, it may be desirable to occlude an anatomical structure by placing an occlusion device, such as an occlusion clip, on the anatomical structure. For example, in some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA, such as by using an occlusion clip. U.S. Pat. Nos. 8,636,754; 9,017,349; 9,861,371; 9,883,867; 9,901,351; 9,901,352; and 10,201,352; and U.S. Patent Application Publication No. 2019/0142428, relate to LAA occlusion devices and methods and are incorporated by reference herein.

The present disclosure contemplates that, in some circumstances, it may be difficult to position an occlusion clip at the desired location on a left atrial appendage at least in part due to the soft and flexible nature of the left atrial appendage. Particularly when the heart is accessed in a minimally invasive manner via one or more small incisions, positioning an occlusion clip on the left atrial appendage may be challenging. In some circumstances, it may be helpful to manipulate and/or apply traction to the left atrial appendage to facilitate placement of a left atrial appendage occlusion clip. The present disclosure contemplates, however, that some known surgical grasping devices, such as those which include teeth or that grasp tissue with large forces, may risk damage to the relatively fragile left atrial appendage tissue causing the tissue to rupture and possibly irreparable damage to the heart. Accordingly, the present disclosure contemplates that, in connection with some left atrial appendage exclusion procedures, it may be advantageous to manipulate the left atrial appendage utilizing a device capable of atraumatically and securely engaging the left atrial appendage.

It is an aspect of the present disclosure to provide a method of positioning an occlusion clip proximate a left atrial appendage including creating an access port allowing communication between an exterior of a human body and an interior of the human body that exposes the left atrial appendage; delivering a suction grasper via the access port, the suction grasper including opposing jaws each having a suction port; delivering an occlusion clip via the access port; grasping the left atrial appendage via the suction grasper by applying suction to an exterior of the left atrial appendage so that a portion of the left atrial appendage interposes the opposing jaws while suction is applied via the suction ports; repositioning the suction grasper to tension the left atrial appendage; clamping a base of the left atrial appendage using the occlusion clip while the suction grasper applies tension to the left atrial appendage; and/or disconnecting the suction grasper from the left atrial appendage and egressing the suction grasper via the access port to the exterior of the human body.

In a detailed embodiment, the opposing jaws of the suction grasper may be resiliently connected to one another. Grasping the left atrial appendage may include repositioning at least one of the opposing jaws with respect to the another of the opposing jaws.

In a detailed embodiment, the opposing jaws of the suction grasper may be repositionably coupled to one another so that at least a first of the opposing jaws is independently repositionable with respect to at least a second of the opposing jaws. Grasping the left atrial appendage may include repositioning at least one of the opposing jaws with respect to the another of the opposing jaws.

In a detailed embodiment, creating the access point may include making a sub-xiphoid incision. Creating the access point may include making a sub-costal incision. Creating the access point may include inserting at least one of a sleeve and a cannula into an incision.

In a detailed embodiment, delivering the occlusion clip may include inserting a clip applier, operatively coupled to the occlusion clip, via the access port. The suction grasper may include a malleable shaft and/or the method further comprises bending the shaft. Grasping the left atrial appendage via the suction grasper may include operating a jaw actuator disposed on a handle of the suction grasper to articulate at least one of the opposing jaws.

It is an aspect of the present disclosure to provide a surgical grasping device including an elongated shaft including a first jaw repositionably mounted to a second jaw, each of the first jaw and the second jaw including a suction orifice; and/or a suction lumen in extending along the elongated shaft and in fluid communication with the suction orifices of the first and second jaws.

In a detailed embodiment, the surgical grasping device may include a controller operatively coupled to the elongated shaft generally opposite the first and second jaws, the controller including a first actuator operatively coupled to at least one of the first and second jaws, the first actuator being repositionably mounted with respect to a housing of the controller in order to change a distance between the first and second jaws. The controller may include a second actuator operatively coupled to the elongated shaft and being repositionably mounted with respect to the housing of the controller in order to change a shape of the elongated shaft. The controller may include a third actuator repositionably mounted with respect to the housing of the controller in order to provide selective fluid communication between the suction lumen and a suction source.

In a detailed embodiment, at least one of the first jaw and the second jaw may include a plurality of suction orifices each comprising an atraumatic projection and in fluid communication with the suction lumen. At least one of the first jaw and the second jaw may include a plurality of suction orifices each comprising an elongated rib oriented longitudinally along a dominant dimension of the at least one of the first and second jaws. At least one of the first jaw and the second jaw may include a plurality of suction orifices each comprising a recessed opening that is in fluid communication with the suction lumen. At least one of the first jaw and the second jaw may include a plurality of suction orifices each comprising an elongated trough oriented longitudinally along a dominant dimension of the at least one of the first and second jaws. At least one of the first jaw and the second jaw may include a plurality of suction orifices interposed by at least one atraumatic projection.

In a detailed embodiment, a resilient bridge may repositionably couple the first jaw to the second jaw. The first jaw may be mechanically linked and repositionably coupled to the second jaw.

It is an aspect of the present disclosure to provide a clip application system including a surgical grasping device as described above and a clip applier.

It is an aspect of the present disclosure to provide a surgical grasping device including a shaft operatively coupled to a first pad and a second pad, where at least one of the first pad and the second pad is configured to be repositionable to modify a distance between the first and second pads; a suction lumen extending along the shaft and in fluid communication with at least one opening exposed to an interior of at least one of the first pad and the second pad; and/or a hand-held control operatively coupled to the shaft so that the shaft interposes the hand-held control and the first and second pads, the controller configured to be repositioned in order to reposition at least one of the shaft and the first and second pads, where the hand-held control is operatively coupled to the suction tube.

In a detailed embodiment, the suction lumen may include a first suction lumen fluidically connected to the first pad and/or a second suction lumen fluidically connected to the second pad. The suction lumen may be disposed at least partially within the shaft. The suction lumen may be disposed at least partially outside of the shaft. The suction lumen may be disposed coaxially around an outside of the shaft.

In a detailed embodiment, the hand-held control may include a jaw actuator, a shaft actuator, and/or a suction actuator.

It is an aspect of the present disclosure to provide a clip application system including a surgical grasping device as described above and a clip applier.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical devices and related methods, and, more specifically, devices for manipulating and/or applying traction to anatomical structures, such as a left atrial appendage of a heart, and related methods. Some example embodiments according to at least some aspects of the present disclosure may be particularly useful in connection with left atrial appendage occlusion procedures, such as to treat cardiac arrhythmias like atrial fibrillation, for the reasons discussed above in the Introduction section and the patent references incorporated by reference herein.

Figure 1:
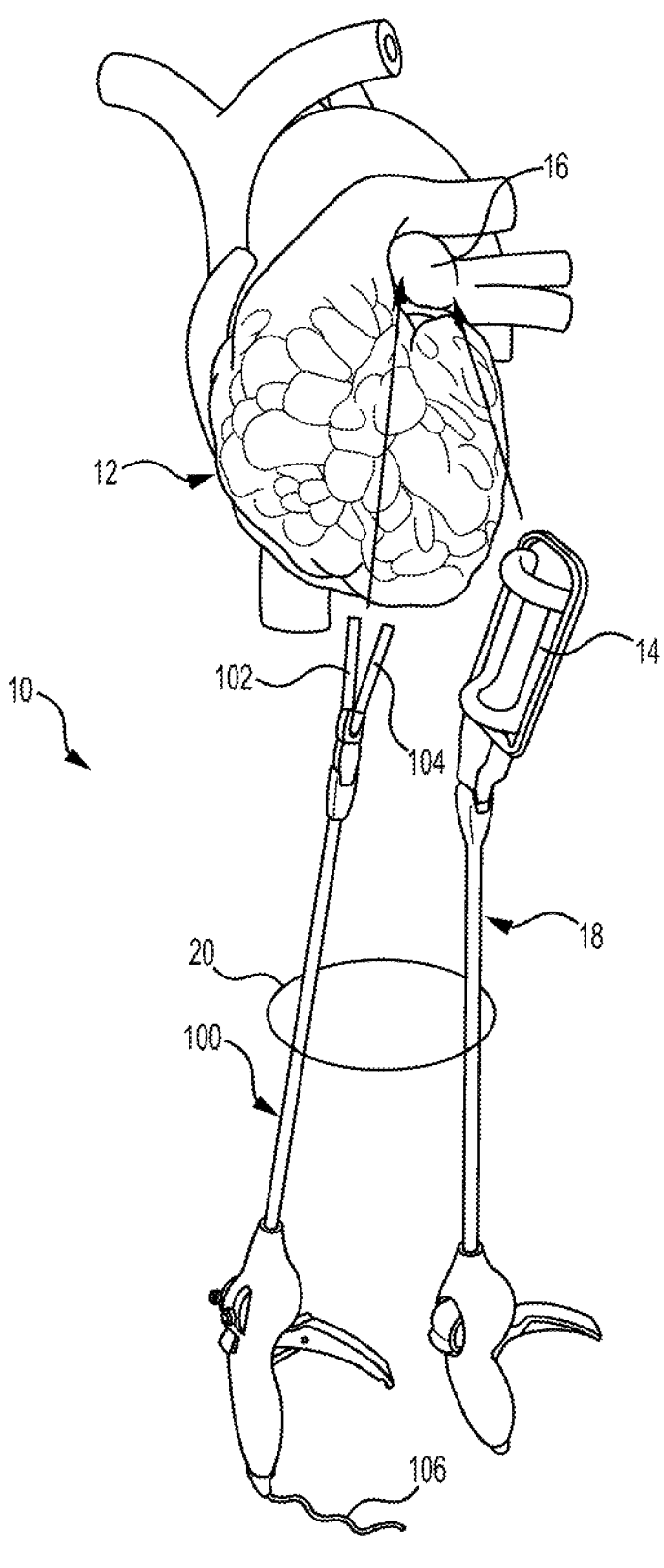
FIG. 1 is a schematic view of an example clip application system and a heart.

FIG. 1 is a schematic view of an example clip application system 10 and a heart 12, according to at least some aspects of the present disclosure. Generally, the clip application system 10 may be used in connection with applying an occlusion clip 14, such as onto the left atrial appendage 16 of the heart 12. As used herein, "occlusion clip" may refer broadly to any occlusion device that is applied to an occludable anatomical structure in a generally similar manner.

The clip application system 10 may include a clip applier 18, such as the AtriClip PRO device available from Atri-Cure, Inc. of Mason, Ohio, which may be configured to position and/or deploy the occlusion clip 14 proximate the left atrial appendage 16. Generally, some example occlusion clips 14 and/or clip appliers 18 may be generally similar to those described in the patent references incorporated by reference herein, and may be operated in generally similar manners. Example occlusion clips 14 may include open-ended occlusion clips and closed-ended occlusion clips.

The clip application system 10 may include a suction grasper 100. The suction grasper 100 may be configured to engage the left atrial appendage 16, which may facilitate atraumatically stabilizing, manipulating, and/or applying traction to the left atrial appendage 16, such as in connection with positioning the occlusion clip 14 using the clip applier 18. As used herein, "traction" may refer to application of a tension force to an anatomical structure by a surgical device. The suction grasper 100 may be used to mechanically grasp the left atrial appendage 16 between a first jaw 102 and a second jaw 104 and/or may utilize suction (e.g., provided via suction line 106). In some example embodiments, both the clip applier 18 and the suction grasper 100 may access the heart 12 via the same access port 20. Generally, the access port 20 may include an incision providing access from an exterior of the patient's body to an interior of the patient's body, such as a sub-xiphoid incision, and/or a cannula or sleeve.

Figure 2:
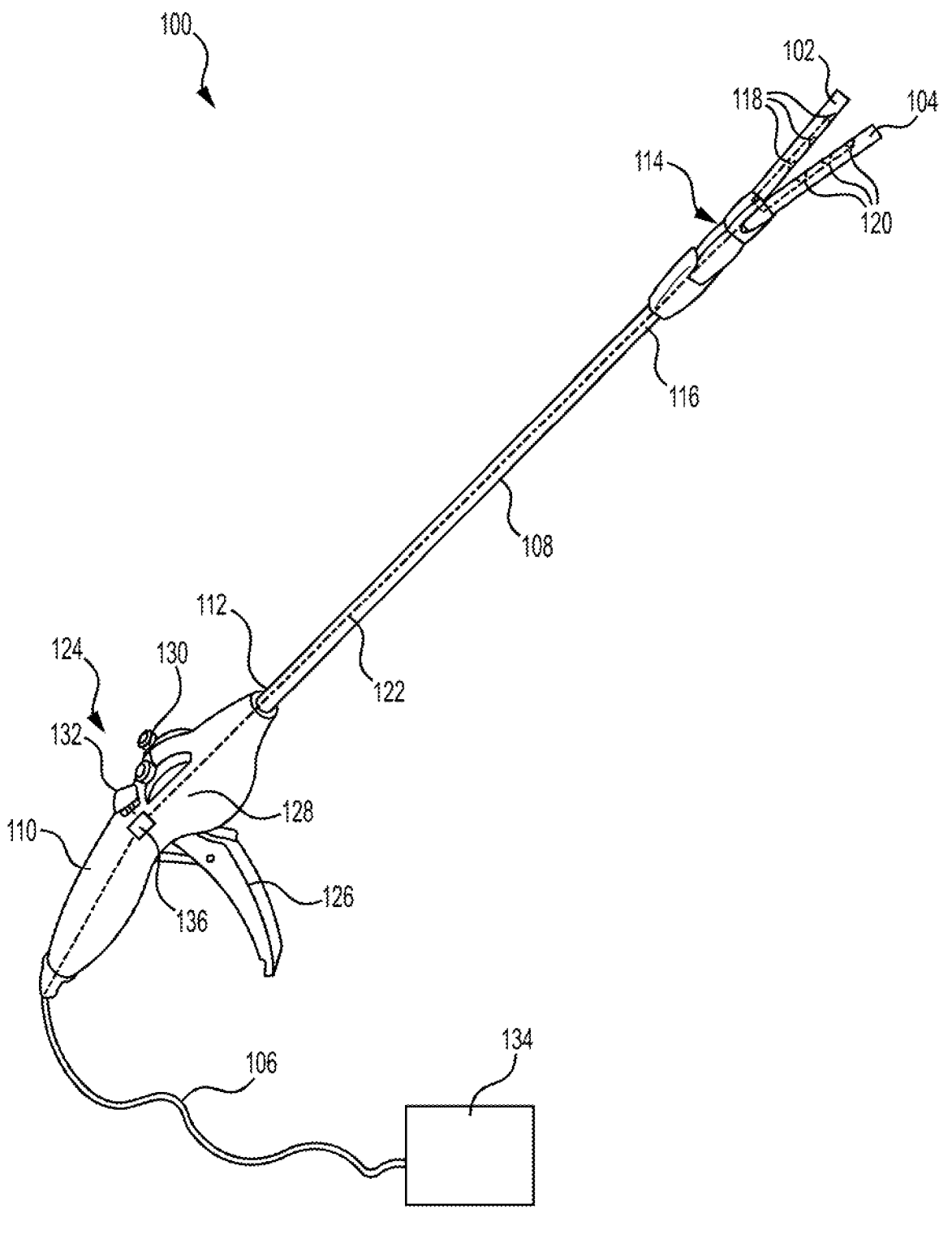
FIG. 2 is a schematic view of an example suction grasper.

FIG. 2 is a schematic view of an example suction grasper 100, according to at least some aspects of the present disclosure. The suction grasper 100 may include an elongated shaft 108, a handle 110 disposed at a proximal end portion 112 of the shaft 108, and/or an end effector 114 disposed at a distal end portion 116 of the shaft 108. As used herein, "distal" may refer generally to the direction towards the portion of a surgical device that is inserted into a patient's body, and "proximal" may refer generally to the direction towards the portion of a surgical device that remains outside of the patient's body. The end effector 114 may include the first jaw 102 and the second jaw 104, which may extend generally distally from the shaft 108.

In some example embodiments, the jaws 102, 104 may be repositionably coupled to one another so that at least one of the jaws 102, 104 is independently repositionable with respect to at least the other of the jaws 102, 104. For example, the first jaw 102 may be mechanically linked to and/or may be repositionably coupled to the second jaw 104, such as by a mechanism in the end effector 114.

In some example embodiments, the first jaw 102 may include one or more suction ports or orifices 118. Similarly, the second jaw may include one or more suction ports or orifices 120. The suction orifices 118, 120 may be in fluid communication with a suction lumen 122, which may extend along the shaft 108. In some example embodiments, the suction lumen 122 may be disposed at least partially within the shaft 108.

The shaft 108 may be substantially rigid (e.g., generally not bendable), generally flexible, substantially malleable (e.g., plastically deformable), and/or steerable. For example, the shaft 108 may be bendable in one or more curves in one or more planes, which may facilitate positioning of the end effector 114 as desired during a surgical procedure. The shaft 108 may be configured to transmit torque between the handle 110 and the end effector 114.

In some example embodiments, the handle 110, which may be configured to be hand-held, may include a controller 124, which may be configured to allow an operator to control one or more aspects of the suction grasper 100. For example, the controller 124 may include a jaw actuator 126, which may be repositionably mounted with respect to a housing 128 of the controller 124 and/or which may be operable to change the distance between the first jaw 102 and the second jaws 104. For example, the jaw actuator 126 may be operable to articulate at least one of the jaws 102, 104 to open and/or close the jaws 102, 104. The patent references incorporated by reference herein describe various suitable example mechanisms for opening and closing jaws.

In some example embodiments, the controller 124 may include a shaft actuator 130, which may be repositionably mounted with respect to the housing 128 and/or which may be operable to change the shape of the elongated shaft 108. For example, the shaft actuator 130 may be operable to steer the shaft 108 about one or more axes.

In some example embodiments, the controller 124 may include a suction actuator 132, which may be repositionably mounted with respect to the housing 128 and/or which may be operable to provide selective fluid communication between the suction lumen 122 and a suction source 134. For example, the suction actuator 132 may selectively open and shut a valve 136 disposed fluidically between the suction source 134 (e.g., a vacuum pump) and the suction lumen 122.

Figure 3:
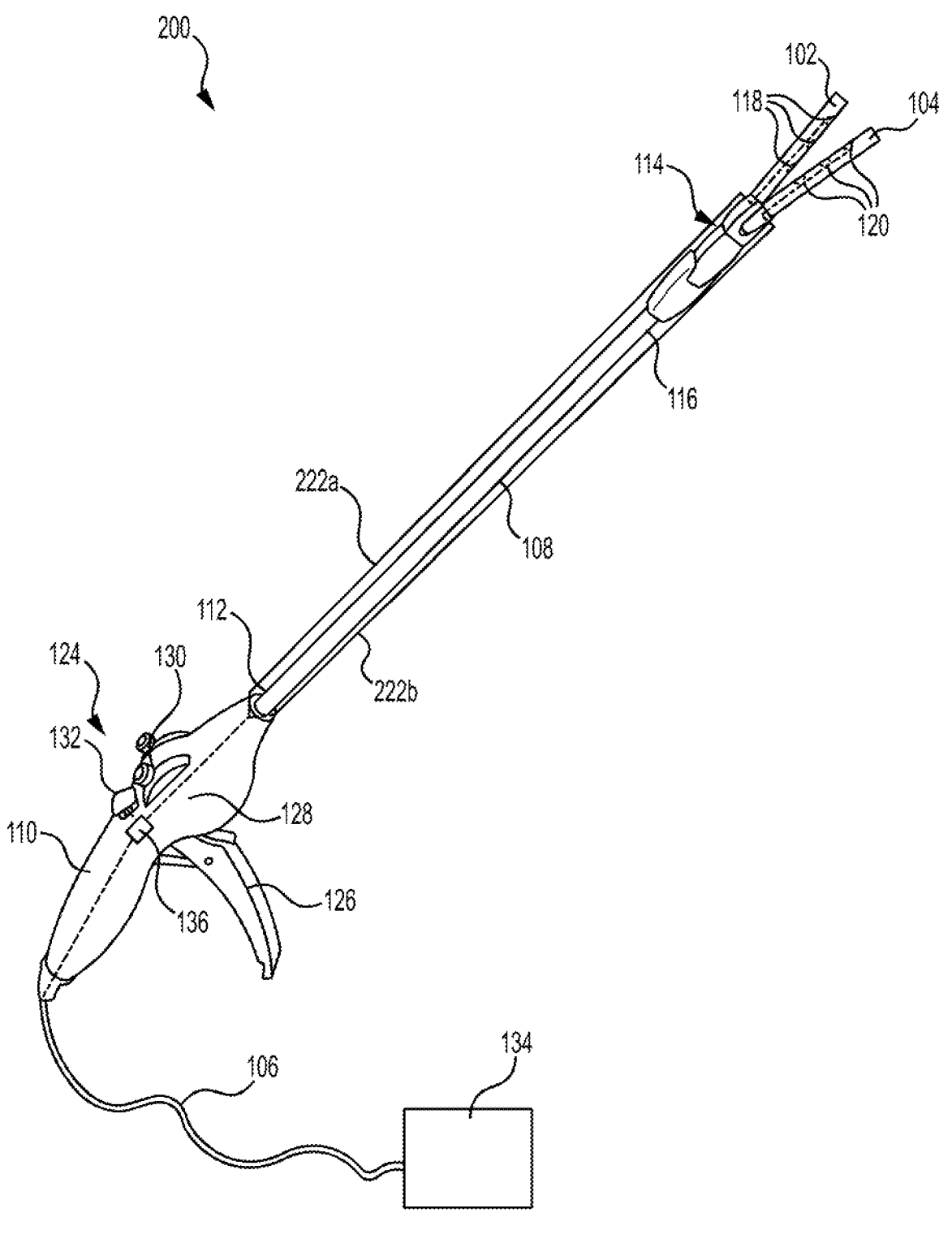
FIG. 3 is a schematic view of an alternative example suction grasper.

FIG. 3 is a schematic view of an alternative example suction grasper 200, according to at least some aspects of the present disclosure. The suction grasper 200 shown and described with respect to FIG. 3 is generally similar to the suction grasper 100 shown and described with respect to FIGS. 1 and 2. Generally, the suction grasper 200 may be substituted for the suction grasper 100 in various embodiments according to at least some aspects of the present disclosure, such as the clip application system 10 described above. Like reference numerals refer to like structure shown and described above. Unless specifically indicated, the description of the structure and function or methodology of corresponding components with respect to the suction grasper 100 generally applies to the suction grasper 200. Therefore, repeated explanation of previously described structure and function or methodology is not necessary.

In some example embodiments, the suction grasper 200 may include one or more suction lumens 222a, 222b that are disposed at least partially outside of the shaft 108, such as generally alongside the exterior of the shaft 108. Suction lumen 222a may be fluidically coupled to the suction orifices 118 of the first jaw 102 and/or suction lumen 222b may be fluidically coupled to the suction orifices 120 of the second jaw 104.

Figure 4:
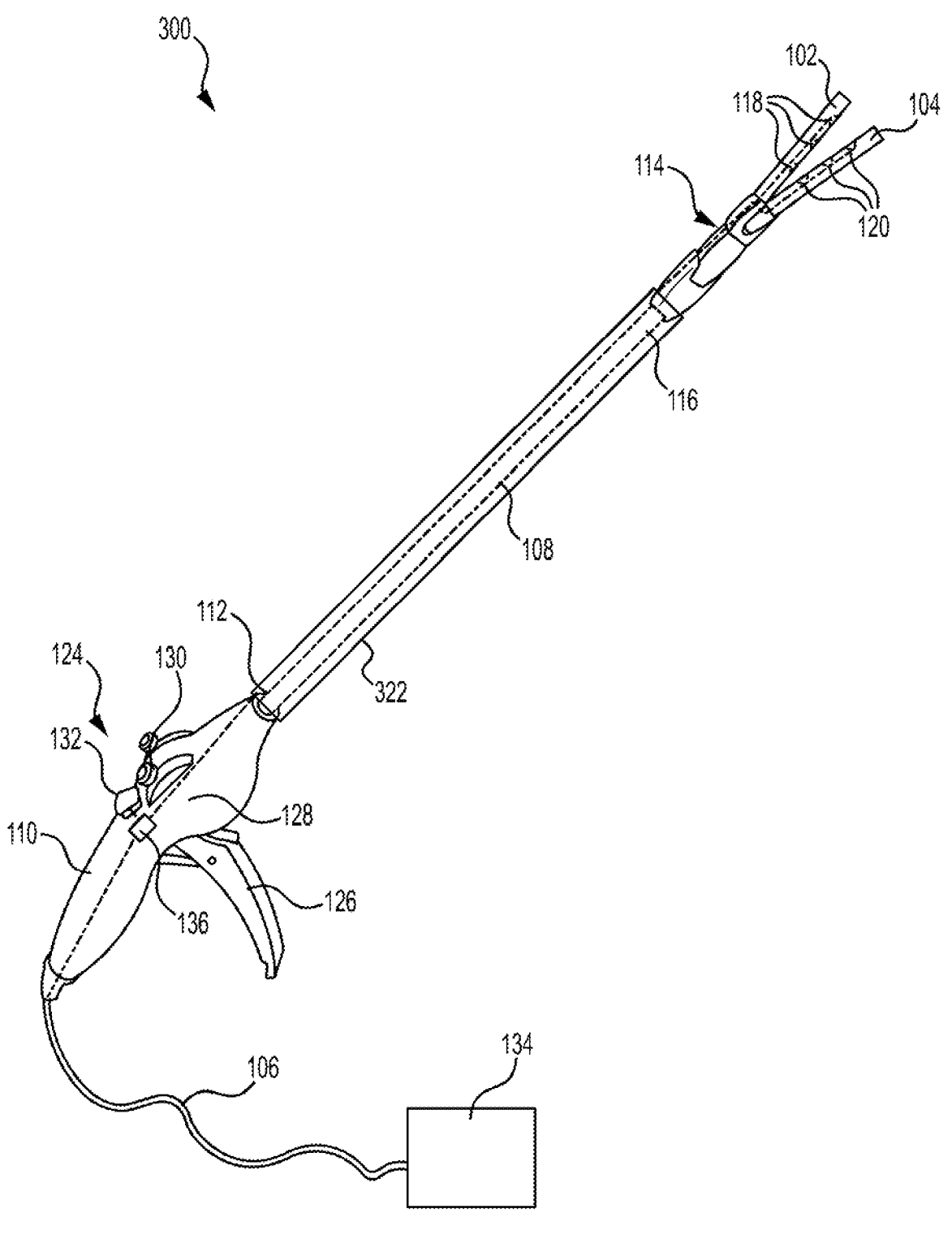
FIG. 4 is a schematic view of an alternative example suction grasper.

FIG. 4 is a schematic view of an alternative example suction grasper 300, according to at least some aspects of the present disclosure. The suction grasper 300 shown and described with respect to FIG. 4 is generally similar to the suction graspers 100, 200 shown and described with respect to FIGS. 1-3. Generally, the suction grasper 300 may be substituted for the suction graspers 100, 200 in various embodiments according to at least some aspects of the present disclosure, such as the clip application system 10 described above. Like reference numerals refer to like structure shown and described above. Unless specifically indicated, the description of the structure and function or methodology of corresponding components with respect to the suction graspers 100, 200 generally applies to the suction grasper 300. Therefore, repeated explanation of previously described structure and function or methodology is not necessary.

In some example embodiments, the suction grasper 300 may include a suction lumen 322 that is disposed generally coaxially around the outside of the shaft 108. The suction lumen 322 may be fluidically coupled to the suction orifices 118 of the first jaw 102 and/or the suction orifices 120 of the second jaw 104.

Figures 5, 6:
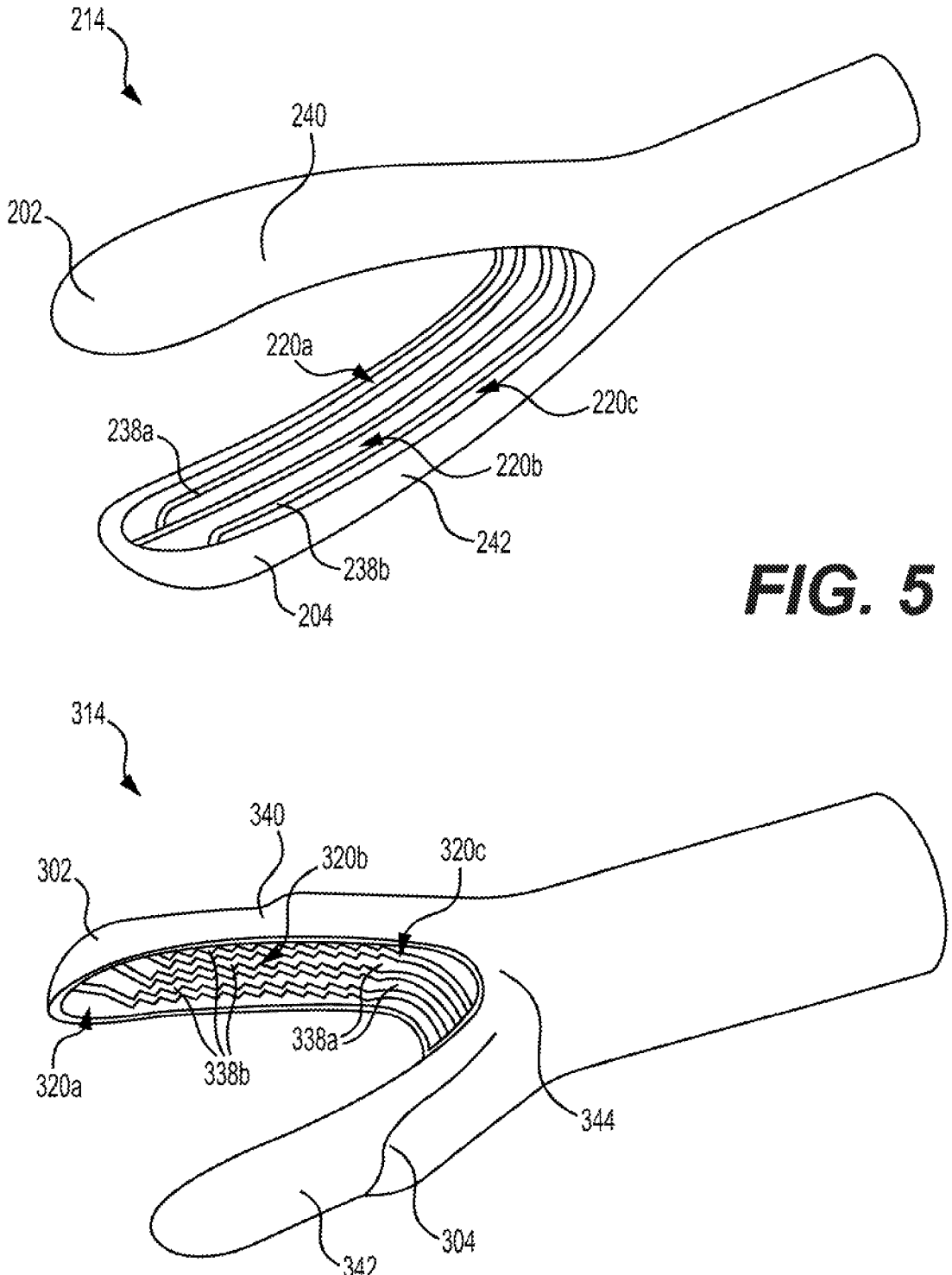
FIG. 5 is an isometric view of an alternative example end effector.
FIG. 6 is an isometric view of an alternative example end effector.

FIG. 5 is an isometric view of an alternative example end effector 214, according to at least some aspects of the present disclosure. The end effector 214 shown and described with respect to FIG. 5 is generally similar to the end effector 114 shown and described with respect to FIGS. 1 and 2. Generally, the end effector 214 may be substituted for the end effector 114 in various embodiments according to at least some aspects of the present disclosure, such as the suction grasper 100 described above. Like reference numerals refer to like structure shown and described above. Unless specifically indicated, the description of the structure and function or methodology of corresponding components with respect to the end effector 114 generally applies to the end effector 214. Therefore, repeated explanation of previously described structure and function or methodology is not necessary.

The jaws 202, 204 may be repositionably coupled to one another so that at least one of the jaws 202, 204 is independently repositionable with respect to at least the other of the jaws 202, 204. For example, the first jaw 202 may be mechanically linked to and/or may be repositionably coupled to the second jaw 204.

One or both of the jaws 202, 204 may include one or more suction ports or orifices 220a, 220b, 220c. The second jaw 204 is shown and described; however, the first jaw 202 may include corresponding structures. In this example embodiment, the suction orifices 220a, 220b, 220c are fluidically connected, such as near the distal end of the second jaw 204. In some example embodiments, the suction orifices 220a, 220b, 220c may be substantially separate. The suction orifices 220a, 220b, 220c may be in fluid communication with the suction lumen 122 (FIG. 2).

In this example embodiment, each of the suction orifices 220a, 220b, 220c comprises and/or is at least partially defined by an atraumatic projection, such as an elongated rib 238a, 238b. The elongated ribs 238a, 238b may be oriented generally longitudinally along a dominant dimension of the jaws 202, 204. The elongated ribs 238a, 238b may interpose the suction orifices 220a, 220b, 220c and/or may at least partially define the suction orifices 220a, 220b, 220c as elongated troughs that may be oriented generally longitudinally along a dominant dimension of the jaws 202, 204.

FIG. 6 is an isometric view of an alternative example end effector 314, according to at least some aspects of the present disclosure. The end effector 314 shown and described with respect to FIG. 6 is generally similar to the end effectors 114, 214 shown and described with respect to FIGS. 1, 2, and 5. Generally, the end effector 314 may be substituted for the end effectors 114, 214 in various embodiments according to at least some aspects of the present disclosure, such as the suction grasper 100 described above. Like reference numerals refer to like structure shown and described above. Unless specifically indicated, the description of the structure and function or methodology of corresponding components with respect to the end effectors 114, 214 generally applies to the end effector 314. Therefore, repeated explanation of previously described structure and function or methodology is not necessary.

The jaws 302, 304 may be repositionably coupled to one another so that at least one of the jaws 302, 304 is independently repositionable with respect to at least the other of the jaws 302, 304. For example, the first jaw 302 may be mechanically linked to and/or may be repositionably coupled to the second jaw 304.

One or both of the jaws 302, 304 may include one or more suction ports or orifices 320a, 320b, 320c. The first jaw 302 is shown and described; however, the second jaw 304 may include corresponding structures. In this example embodiment, the suction orifices 320a, 320b, 320c are fluidically connected. In some example embodiments, the suction orifices 320a, 320b, 320c may be substantially separate. The suction orifices 320a, 320b, 320c may be in fluid communication with the suction lumen 122 (FIG. 2).

In this example embodiment, each of the suction orifices 320a, 320b, 320c comprises and/or is at least partially defined by an atraumatic projection, such as an elongated rib 338a and/or a post 338b. The elongated ribs 338a may be oriented generally longitudinally along a dominant dimension of the jaws 302, 304. The elongated ribs 338a may interpose the suction orifices 320c and/or may at least partially define the suction orifices 320c as elongated troughs that may be oriented generally longitudinally along a dominant dimension of the jaws 302, 304. The posts 338b may interpose the suction orifices 320b and/or may be spaced apart to provide a plurality of atraumatic projections. In some example embodiments, at least a portion of the jaw 302 defining a suction orifice 320a may include few or no projections.

As shown in FIGS. 5 and 6, some example embodiments may be constructed with a first pad 240, 340 comprising the first jaw 202, 302 and/or a second pad 242, 342 comprising the second jaw 204, 304. In some example embodiments, the pads 240, 242, 340, 342 may be constructed of a flexible material that is disposed about a relatively rigid structure forming the jaws 202, 204, 302, 304. In some example embodiments, the pads 204, 242, 340, 342 may be substantially flexible and/or without a relatively rigid internal structure.

In some example embodiments, the jaws 102, 104, 202, 204, 302, 304 may be articulable between open and closed configurations, such as by operation of the jaw actuator 126 (FIG. 2) and/or a jaw articulation mechanism. In some example embodiments, the jaws 102, 104, 202, 204, 302, 304 may be repositionable with respect to one another, but may not be articulable by the action of an actuator and/or a mechanism. In some example embodiments, the jaws 102, 104, 202, 204, 302, 304 may be resiliently connected to each other. For example, the jaws 302, 304 of the end effector 314 of FIG. 6 may be resiliently connected by a resilient bridge 344 that is configured to bias the jaws 302, 304 generally toward an open configuration. In some such embodiments, the jaws 302, 304 may be drawn towards a closed configuration when suction is applied to the suction orifices 320a, 320b, 320c and the jaws 302, 304 engage the tissue.

In some example embodiments, the access port 20 may be utilized for a scope, such as an endoscope. As used herein, "scope" may refer to an optical device used to observe an area within a patient's body and may include rigid or flexible endoscopes, laparoscopes, arthroscopes, bronchoscopes, ureteroscopes, etc. A scope may include a lighting feature and/or may be utilized with a separate lighting device, either of which may be used to illuminate the field of view of the scope. Further, scopes as described herein may include "chip on the tip" configurations in which a video sensor and/or a light source are permanently embedded into a device, such as proximate the distal end of an instrument.

FIGS. 7-12 are anterior perspective views of a heart 12 illustrating an example method of using a clip application system 10 to apply an occlusion clip 14 on a left atrial appendage 16, according to at least some aspects of the present disclosure. It will be appreciated that although the following description focuses on a particular example embodiment of the clip application system 10, various other example embodiments including alternative features according to at least some aspects of the present disclosure may be utilized in a similar manner.

Figure 7:
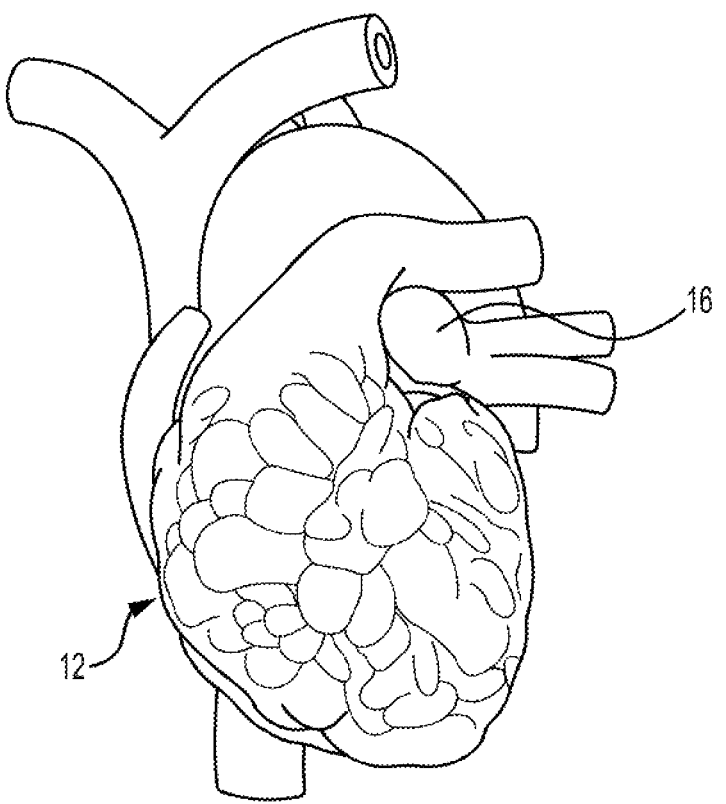
FIGS. 7-12 are anterior perspective views of a heart illustrating an example method of using a clip application system to apply an occlusion clip on a left atrial appendage; all in accordance with at least some aspects of the present disclosure.
Figure 7:
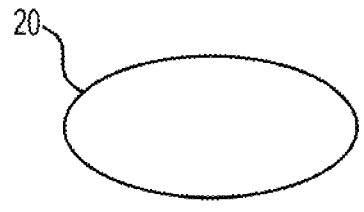

Referring to FIG. 7, the access port 20 may be established, allowing communication between an exterior 22 of a human body and an interior 24 of the human body and exposing the left atrial appendage 16. The access port 20 may be created, for example, by making an incision (e.g., sub-xiphoid or sub-costal) and/or may include inserting a sleeve or cannula into the incision.

Figure 8:
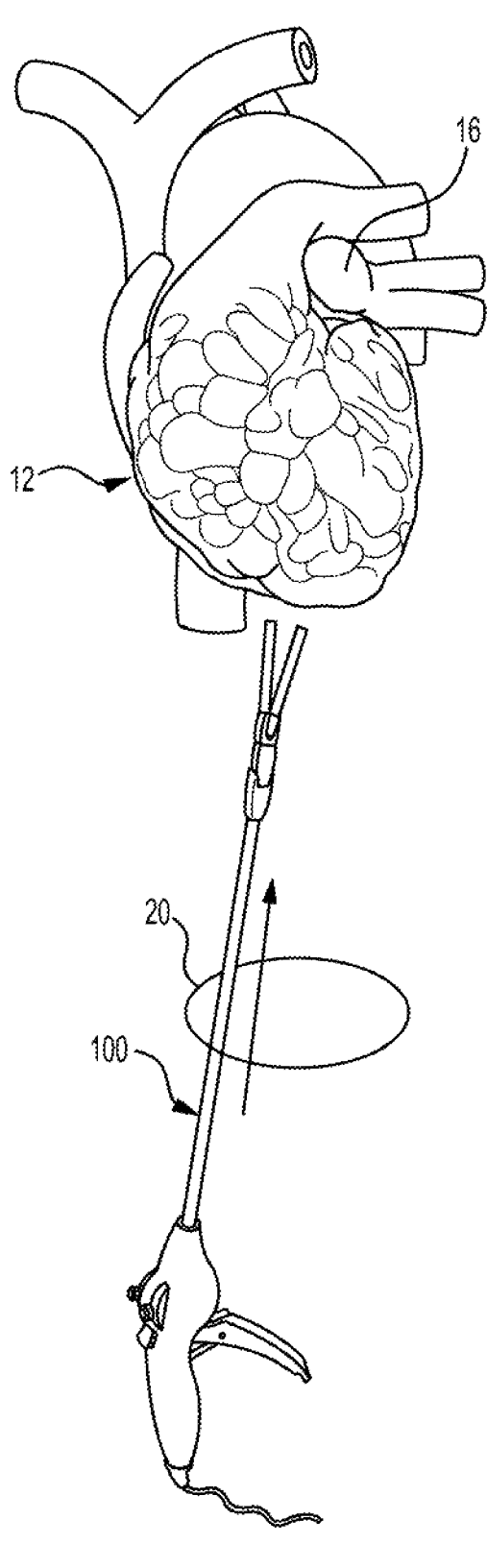

Referring to FIG. 8, the suction grasper 100 may be delivered via the access port 20. As described above with reference to FIG. 2, the suction grasper 100 may include opposing jaws 102, 104, each having at least one suction port 118, 120.

Figure 9:
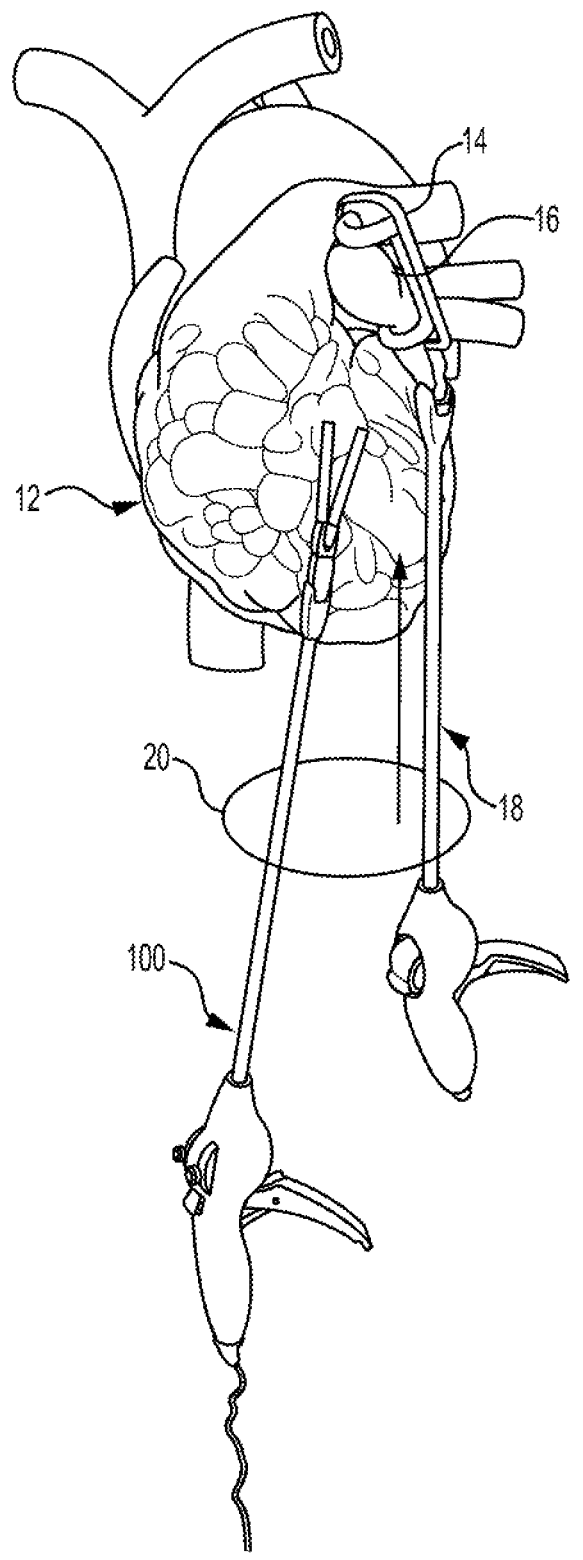

Referring to FIG. 9, the occlusion clip 14 may be delivered via the access port 20, such as by inserting a clip applier 18 carrying the occlusion clip 14.

Figure 10:
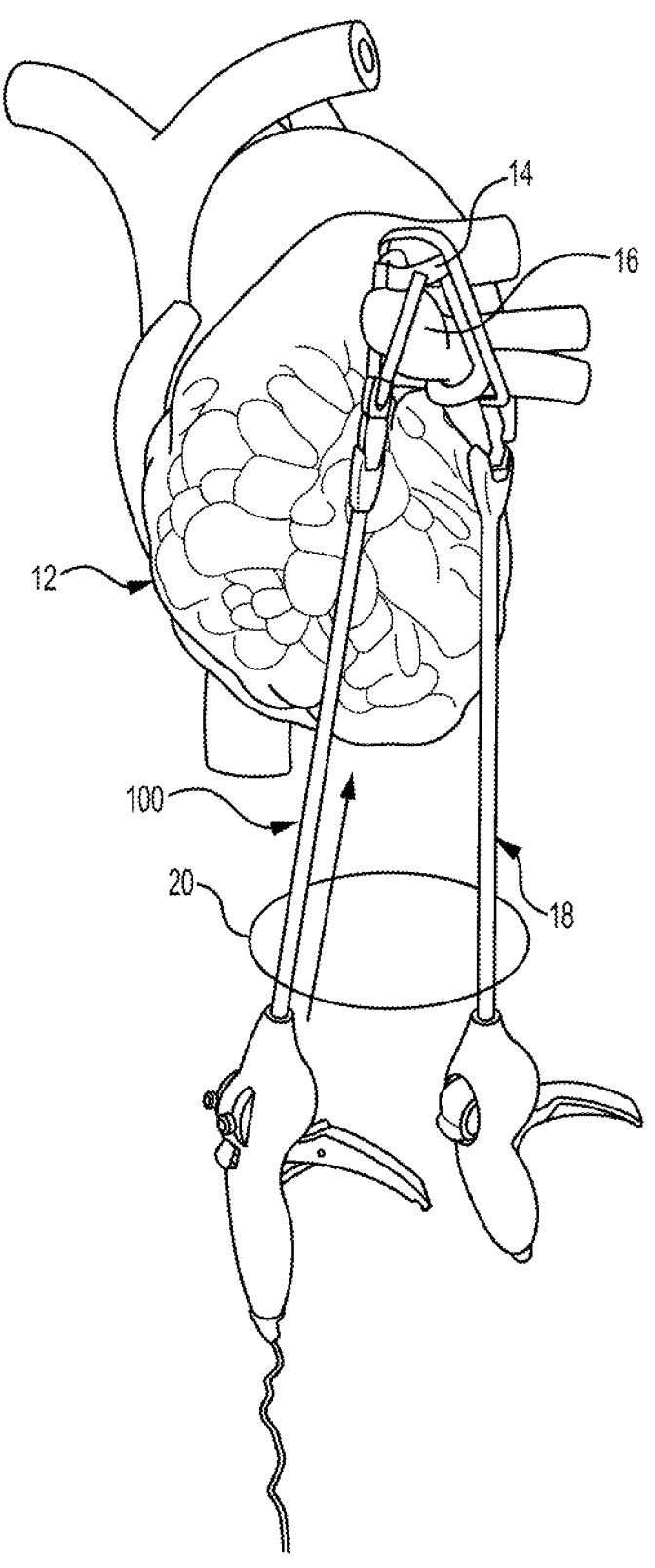

Referring to FIG. 10, the left atrial appendage 16 may be grasped by the suction grasper 100, such as via the suction grasper 100 applying suction to an exterior of the left atrial appendage 16 so that a portion of the left atrial appendage 16 interposes the opposing jaws 102, 104 while suction is applied via the suction ports 118, 120 (FIG. 2).

Figure 11:
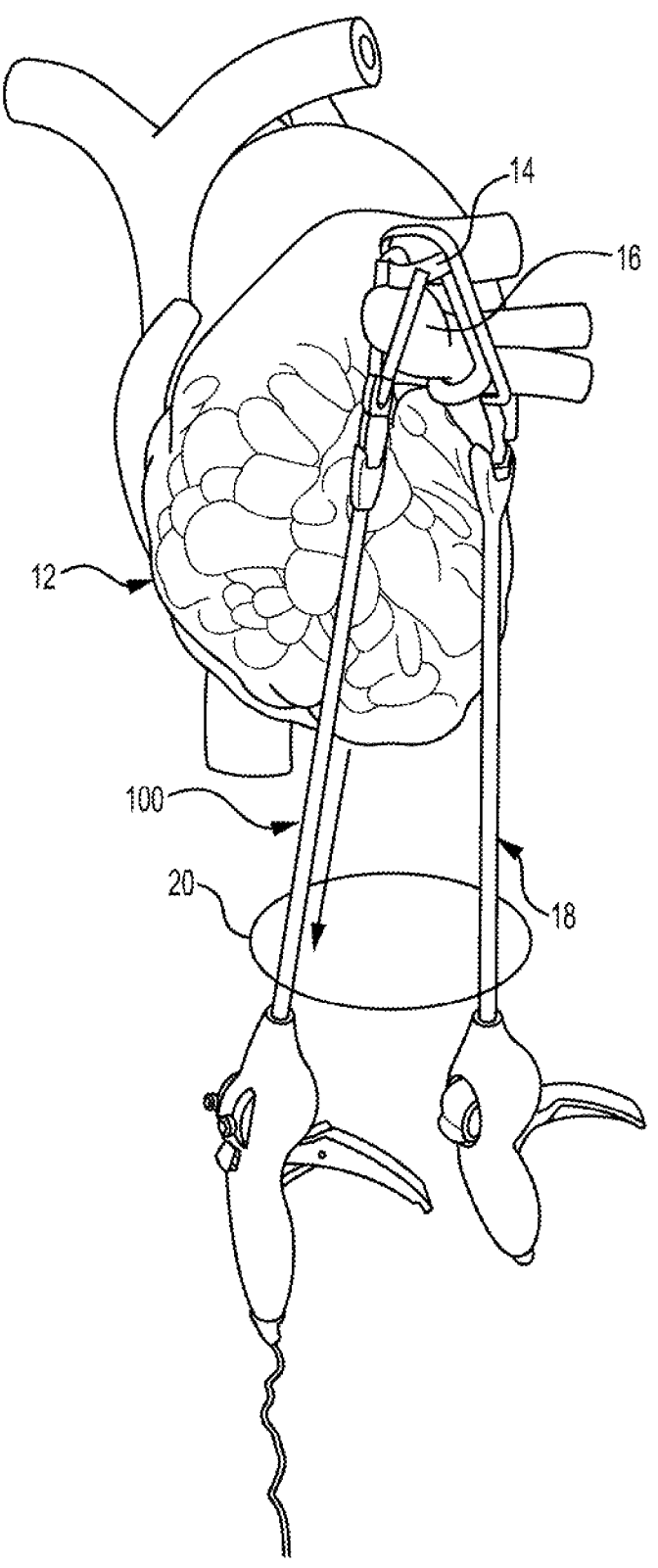

Referring to FIG. 11, the suction grasper 100 may be repositioned to tension (e.g., apply traction to) the left atrial appendage 16. The clip applier 18 may be repositioned as needed to position the occlusion clip 14 as desired, such as proximate a base of the left atrial appendage. The base of the left atrial appendage 16 may be clamped using the occlusion clip 14 while the suction grasper 100 applies tension (e.g., traction) to the left atrial appendage 16.

Figure 12:
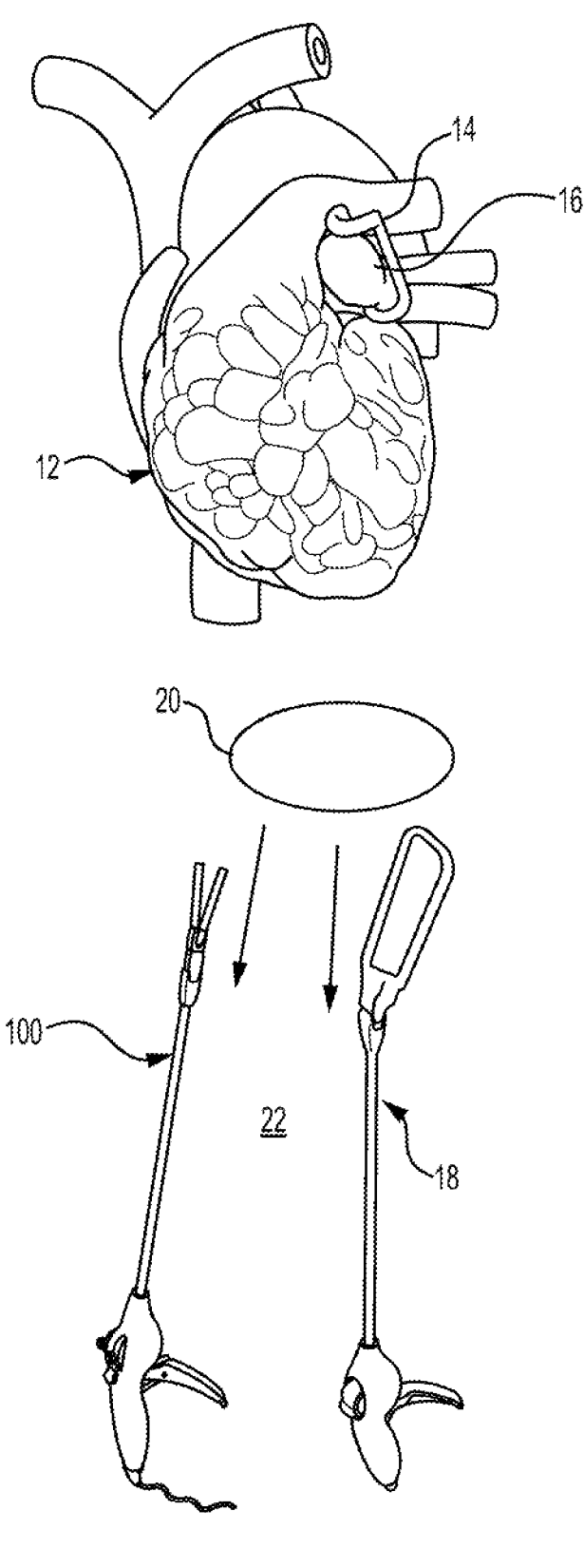

Referring to FIG. 12, the occlusion clip 14 may be deployed. Before, during, or after deployment of the occlusion clip 14, the suction grasper 100 may be disconnected from the left atrial appendage 16 and/or egressed via the access port 20 to the exterior 22 of the human body. The clip applier 18 may be egressed via the access port to the exterior 22 of the human body. The occlusion clip 14 may remain on the LAA 16 and/or may be operative to exclude the LAA 16. The incision(s) may be closed and/or one or more drains may be placed.

Example embodiments according to at least some aspects of the present disclosure may be configured for use with any desired occlusion devices, including those disclosed in the patent references incorporated by reference herein. Example embodiments according to at least some aspects of the present disclosure may be utilized in connection with surgical procedures, such as occlusion procedures, involving any occludable structure in a patient's body.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A method of positioning an occlusion clip proximate a left atrial appendage, the method comprising:
   creating an access port allowing communication between an exterior of a human body and an interior of the human body that exposes the left atrial appendage;
   delivering a suction grasper via the access port, the suction grasper including opposing jaws each having a suction port;
   delivering the occlusion clip via the access port;
   grasping the left atrial appendage via the suction grasper by applying suction to an exterior of the left atrial appendage so that a portion of the left atrial appendage interposes the opposing jaws while suction is applied via the suction ports;
   repositioning the suction grasper to tension the left atrial appendage;
   overcoming a bias of the occlusion clip to open the occlusion clip, where the occlusion clip is biased closed, and position dual beams of the occlusion clip at least partially around the left atrial appendage;
   discontinuing overcoming of the bias of the occlusion clip to clamp a base of the left atrial appendage using the dual beams of the occlusion clip while the suction grasper applies tension to the left atrial appendage; and
   disconnecting the suction grasper from the left atrial appendage and egressing the suction grasper via the access port to the exterior of the human body.

2. The method of claim 1,
   wherein the opposing jaws of the suction grasper are resiliently connected to one another; and wherein grasping the left atrial appendage comprises repositioning at least one of the opposing jaws with respect to the another of the opposing jaws.

3. The method of claim 1,
   wherein the opposing jaws of the suction grasper are repositionably coupled to one another so that at least a first of the opposing jaws is independently repositionable with respect to at least a second of the opposing jaws; and
   wherein grasping the left atrial appendage comprises repositioning at least one of the opposing jaws with respect to the another of the opposing jaws.

4. The method of claim 1, wherein creating the access point comprises making a sub-xiphoid incision.

5. The method of claim 1, wherein creating the access point comprises making a sub-costal incision.

6. The method of claim 1, wherein creating the access point comprises inserting at least one of a sleeve and a cannula into an incision.

7. The method of claim 1, wherein delivering the occlusion clip comprises inserting a clip applier, operatively coupled to the occlusion clip, via the access port.

8. The method of claim 1,
   wherein the suction grasper comprises a malleable shaft; and
   wherein the method further comprises bending the shaft.

9. The method of claim 1, wherein grasping the left atrial appendage via the suction grasper comprises operating a jaw actuator disposed on a handle of the suction grasper to articulate at least one of the opposing jaws.

10. A method of positioning an occlusion clip proximate a left atrial appendage, the method comprising:
   creating an access port allowing communication between an exterior of a human body and an interior of the human body that exposes the left atrial appendage;
   delivering a suction grasper via the access port, the suction grasper including opposing jaws each having a suction port;
   delivering the occlusion clip via the access port to be positioned at least partially around the left atrial appendage;
   grasping the left atrial appendage via the suction grasper, after the occlusion clip is positioned at least partially around the left atrial appendage, by applying suction to an exterior of the left atrial appendage so that a portion of the left atrial appendage interposes the opposing jaws while suction is applied via the suction ports;
   repositioning the suction grasper to tension the left atrial appendage;
   clamping a base of the left atrial appendage using beams of the occlusion clip while the suction grasper applies tension to the left atrial appendage; and
   disconnecting the suction grasper from the left atrial appendage and egressing the suction grasper via the access port to the exterior of the human body.

11. The method of claim 10, wherein:
   the opposing jaws of the suction grasper are resiliently connected to one another; and
   grasping the left atrial appendage comprises repositioning at least one of the opposing jaws with respect to the another of the opposing jaws.

12. The method of claim 10, wherein:
   the opposing jaws of the suction grasper are repositionably coupled to one another so that at least a first of the opposing jaws is independently repositionable with respect to at least a second of the opposing jaws; and grasping the left atrial appendage comprises repositioning at least one of the opposing jaws with respect to the another of the opposing jaws.

13. The method of claim 10, wherein creating the access point comprises making a sub-xiphoid incision.

14. The method of claim 10, wherein creating the access point comprises making a sub-costal incision.

15. The method of claim 10, wherein creating the access point comprises inserting at least one of a sleeve and a cannula into an incision.

16. The method of claim 10, wherein delivering the occlusion clip comprises inserting a clip applier, operatively coupled to the occlusion clip, via the access port.

17. The method of claim 10, wherein:

the suction grasper comprises a malleable shaft; and the method further comprises bending the shaft.

18. The method of claim 10, wherein grasping the left atrial appendage via the suction grasper comprises operating a jaw actuator disposed on a handle of the suction grasper to articulate at least one of the opposing jaws.

\* \* \* \* \*